United States Patent
Vachon et al.

(10) Patent No.: US 6,934,013 B2
(45) Date of Patent: Aug. 23, 2005

(54) COMPRESSED SYMBOLOGY STRAIN GAGE

(76) Inventors: Reginald Vachon, 1414 Epping Forest Dr., Atlanta, GA (US) 30319; William Ranson, 4015 Devereauz Rd., Columbia, SC (US) 29205

( * ) Notice: Subject to any disclaimer, the term of this patent is extended or adjusted under 35 U.S.C. 154(b) by 266 days.

(21) Appl. No.: 10/223,680

(22) Filed: Aug. 20, 2002

(65) Prior Publication Data

US 2004/0036853 A1 Feb. 26, 2004

(51) Int. Cl.⁷ .............................................. G01B 11/16
(52) U.S. Cl. ......................................... 356/32; 73/800
(58) Field of Search ......................... 356/32–35.5, 11; 73/760, 794, 799, 800, 11; 702/42

(56) References Cited

U.S. PATENT DOCUMENTS

| | | | | |
|---|---|---|---|---|
| 3,474,237 A | * | 10/1969 | Hastings | 702/42 |
| 4,008,960 A | | 2/1977 | Reyblatt | |
| 4,014,613 A | | 3/1977 | Sharpe, Jr. et al. | 356/106 R |
| 4,050,818 A | | 9/1977 | Sharpe, Jr. et al. | 356/32 |
| 4,288,852 A | | 9/1981 | Holland | 364/508 |
| 4,591,996 A | | 5/1986 | Vachon | 364/508 |
| 4,722,600 A | | 2/1988 | Chiang | 356/32 |
| 4,939,354 A | | 7/1990 | Priddy et al. | 235/456 |
| 4,969,106 A | | 11/1990 | Vogel et al. | 364/508 |
| 5,053,609 A | | 10/1991 | Priddy et al. | 235/436 |
| 5,065,331 A | * | 11/1991 | Vachon et al. | 356/35.5 |
| 5,124,536 A | | 6/1992 | Priddy et al. | 235/432 |
| 5,442,729 A | | 8/1995 | Kramer et al. | 395/2.8 |
| 5,531,122 A | * | 7/1996 | Chatham et al. | 73/760 |
| 5,671,042 A | * | 9/1997 | Sciammarella | 356/35.5 |
| 5,726,907 A | * | 3/1998 | Davidson et al. | 702/42 |
| 5,920,383 A | * | 7/1999 | Chen et al. | 356/32 |
| 6,023,334 A | | 2/2000 | Itagaki et al. | 356/376 |
| 6,189,356 B1 | * | 2/2001 | Simeone et al. | 72/53 |
| 6,718,269 B2 | * | 4/2004 | Sinha | 702/42 |

FOREIGN PATENT DOCUMENTS

| | | |
|---|---|---|
| EP | 0 921 371 | 6/1999 |
| JP | 57 125803 | 8/1982 |
| JP | 2002 267422 | 9/2002 |

OTHER PUBLICATIONS

Timoshenko et al.; Theory of Elasticity; McGraw–Hill Book Company, Inc.; 1951; pp. 1–27.

Mathans et al.; A White Paper on two Dimensional Symbols; Because you need information on the fly and on the spot; 1996; p. 1–71.

NASA Technical Handbook; Application of data matrix identification symbols to aerospace parts using direct part marking methods/techniques; NASA–HDBK–6003; 2001; pp. i–vi and 1–42.

Patent Abstracts of Japan, vol. 006, No. 221 (P–153) (Nov. 5, 1982).

Patent Abstracts of Japan, vol. 2003, No. 01 (Jan. 14, 2003).

* cited by examiner

*Primary Examiner*—Gregory J. Toatley, Jr.
*Assistant Examiner*—Layla Lauchman
(74) *Attorney, Agent, or Firm*—Jacobson Holman PLLC (57) ABSTRACT

A compressed symbology strain gage includes a target in the form of a symbolic strain rosette ("SSR"), the target being associated with a body for which strain is to be measured and being adapted to emit a detectable physical quantity; a sensor compatible with and adapted to pre-process the detectable physical quantity emitted by the target and output data representing the physical quantity adapted to receive signals from the target and provide output signals based thereon; a computer program or programs for analyzing the signals data output by the sensor to define the SSR; and for calculating the strain directly on the body based on the pre-processed and analyzed data. The SSR can be defined either a priori by manufacture or a posteriori by identification. A method of measuring strain on an object using the compressed symbology strain gage includes the steps of associating a SSR with an object in such a way that deformation of the SSR and deformation under load of the object bear a one-to-one relationship; identifying the changes in the SSR as a function of time and change in the load applied to the object; and translating the changes in the SSR into strain.

16 Claims, 7 Drawing Sheets

| FIGURE 9A |
|---|
| FIGURE 9B |

COMPRESSED SYMBOLOGY STRAIN GAGE

FIELD OF THE INVENTION

The present invention relates to strain gages, and particularly to a strain gage that can measure strain directly, as well as assess fatigue damage.

BACKGROUND OF THE INVENTION

The strain rosette is a fundamental of analytical strain analysis, as explained in the engineering text "Theory of Elasticity" by Timoshenko and Goodier: The strains, or unit elongations, on a surface are usually most conveniently measured by means of electric-resistance strain gages. The use of these gages is simple when the principal directions are known. One gage is placed along each principal direction and an analog of strain is measured and calibrated to indicate strains $\epsilon_1$, $\epsilon_2$. The principal stresses $\sigma_1$, $\sigma_2$ can then be calculated from Hooke's law, with $\sigma_x=\sigma_1$, and $\sigma_y=\sigma_2$, and with $\sigma_z=0$ on the assumption that there is no stress acting on the surface to which the gauges are attached. Then:

$$(1-v^2)\sigma_1 = E(\epsilon_1 + v\epsilon_2) \text{ and}$$

$$(1-v^2)\sigma_2 = E(\epsilon_2 + v\epsilon_1)$$

When the principal directions are not known in advance, three measurements are needed. Thus, the state of strain is completely determined if $\epsilon_x$, $\epsilon_y$, and $v_{xy}$ can be measured. But since strain gages, and particularly electrical resistance strain gages, measure extensions, and not shearing strain directly, it is convenient to measure the unit elongations in three directions at the point. Such a set of electrical resistance gages is commonly called a "strain rosette" because the gages are arranged in the pattern of a strain rosette; however, "strain rosette" is used here in its original sense (as set forth in the definitions below), rather than to denote a configuration of electrical resistance gages.

A Mohr strain circle can be constructed for a strain rosette, and the differential equations of equilibrium for a small rectangular block of edges h, k, and unity can be derived. If X, Y denote the components of body force per unit volume, the equation of equilibrium for forces in the x-direction is $$(\sigma_x)_1 k - (\sigma_x)_3 k + (\tau_{xy})_2 h - (\tau_{xy})_4 h + Xhk = 0,$$

where $\sigma_x$, $\sigma_y$, and $\tau_{xy}$ refer to the point x, y, the mid-point of the small rectangular block, and where $(\sigma_x)_1$, $(\sigma_x)_3$, etc. denote the values at the mid-points of the faces of the rectangle. The dividing by hk, $$\frac{(\sigma_x)_1 - (\sigma_x)_3}{h} + \frac{(\tau_{xy})_2 h - (\tau_{xy})_4 h}{k} + X = 0$$

If the block is taken smaller and smaller, that is, h→0, h→0, the limit of $[(\sigma_x)_1-(\sigma_x)_3]/k$ is $\partial\sigma_x/\partial x$ by the definition of such a derivative. Similarly, $[(\tau_{xy})_2, -(\tau_{xy})_4]/k$ is $\partial\tau_{xy}/\partial y$. The equation of equilibrium for forces in the y-direction is obtained in the same manner.

Strain measurements made with electrical resistance gages in a rosette pattern are subject to the same errors (thermal output, transverse sensitivity, leadwire resistance effects, etc.) as those made with single-element strain gages.

Letters Patent of U.S. Pat. No. 4,591,996 to Vachon and Ranson discloses optical strain measurement using correlation of speckle patterns reflected from an illuminated optically diffuse surface. The speckle patterns are random signals that are characteristics of the surface area under investigation. Each area of the surface has a unique pattern just as each individual has unique facial characteristics. Correlating the movement of the speckle pattern of a surface undergoing deformation using machine vision to record the speckle pattern movement as a function of time permits the determination of strain.

Technical efforts have continued in the area of optical correlation of surface images to detect strain. Specifically, these efforts include, among other things: (1) optical detection of edges of images on surfaces as well as optical detection of edges of surfaces, (2) optical correlation of dot and other geometric patterns applied to surfaces, and (3) optical correlation of the movement of centroids of geometric patterns applied to surfaces. All of these analytical and experimental efforts have been directed to optical detection of strain.

Single-element strain gages, electrical resistance gages arranged in a rosette pattern employ analog techniques, rather than measuring strain directly. Previous optical correlation techniques calculate strains using a convolution integral, and also do not measure strain directly.

It is to the provision of a strain gage that can measure strain directly, as well as assessing fatigue damage, that the present invention is directed.

BRIEF SUMMARY OF THE INVENTION

Definitions and abbreviations used herein are as follows:

Compressed—the compression of data within a symbol.

Compressed symbol—a compressed symbology symbol.

Compressed symbology—a general term used to describe a category of identification symbols that can be encoded with information, can be marked directly on the surface of a product, or applied to a film or other medium that is in turn bonded to the surface of a product, and can be scaled up or down to fit the application. Their structure is usually a matrix format, resembling a checkerboard.

Edge—a dramatic change in pixel brightness values between regions. It is the point or points that has or have the greatest amount of contrast difference (change in intensity values) between pixels. See "Application of Data Matrix Identification Symbols to Aerospace Parts Using Direct Part Marking Methods/Techniques," NASA-HDBK-6003, Jul. 2, 2001.

Fatigue damage (accumulated damage)—the cumulative or irreversible damage incurred in materials caused by cyclic application of stresses and environments resulting in degradation of load carrying capacity. See "Application of Data Matrix Identification Symbols to Aerospace Parts Using Direct Part Marking Methods/Techniques," NASA-HDBK-6003, Jul. 2, 2001.

Quiet zone—areas of high reflectance (spaces) surrounding a machine readable symbol. Quiet zone requirements may be found in application and symbology specifications. Sometimes called "Clear Area" or "Margin."

Strain rosette—a pattern of intersecting lines on a surface along which linear strains are measured to find stresses at a point (stress at a point is a quantity calculated from data derived from the strain rosette).

SSR—symbolic strain rosette.

Stress at a point—a calculated quantity from the strain rosette data.

Symbolic strain rosette—a strain rosette in the form of a compressed symbol that is defined in terms of its physical dimensions, and more particularly, of the end points of three intersecting line segments that define the strain rosette. The compressed symbol can be a two dimensional bar code matrix or other pattern in which the strain rosette is defined either a priori by manufacture or a posteriori by identification.

Symbology—a machine-readable pattern composed of quiet zone, finder pattern, and symbol characters (which include special functions and error detection and/or correction characters) required by a particular symbology It is a primary object of the present invention to provide a strain gage that measures strain directly, as opposed to measuring strain by analog techniques.

These and other objects of the invention are achieved by provision of a compressed symbology strain gage comprising a target, a sensor, and a computer. The target comprises a symbolic strain rosette ("SSR"), and can be part of an overall image.

The target can be applied directly or indirectly to the surface of a body for which strain is to be measured, or identified in a pre-existing pattern that defines the SSR. The target can be identified by observing naturally occurring marks or objects that define an SSR on a macroscopic or microscopic scale. Whether applied or identified, it can be covered by paint or other material. The target can also be embedded in the object for which strain is to be measured.

In one embodiment of the invention, the SSR can be a strain rosette contained in a "two dimensional bar code," particularly a Data Matrix symbol.

In another embodiment of the invention, the SSR can be identified in a pre-existing overall image.

There are an infinite number of image configurations for the SSR. The SSR can be composed of a plurality of sub-images, each of which has a centroid, and can be monitored by the sensor to correlate the movement of the centroids of the sub-images of the SSR.

The specific SSR must be associated with an object (by application or identification) in such a way that the deformation of the SSR and the deformation under load of the object with which it is associated (that is, to which it is applied or on which it is identified) bear a one-to-one relationship. The target comprising the SSR is monitored—by an optical, magnetic, electromagnetic, acoustic, or other sensor, as appropriate—either on a continuous basis, at random times triggered by an external event, or at predetermined intervals. The images of the SSR are correlated to detect the movement of the centroids of the sub-images of the SSR being used or the sub-images identified in a non-SSR symbol, the movements are quantified and utilized in analytical expressions to determine strain in the directions of the coordinate system used corresponding to the plane of the surface under study. The movement of centroids is detected by a computer-implemented program in accordance with the present invention, which identifies the SSR, correlates the specific symbol/sub images (constituting the SSR) used, determines the displacement of the centroids of the sub-images of the SSR, and utilizes the data obtained as input for strain equations as described hereinafter and to yield and display strain in two dimensions.

The target can naturally emit a detectable physical quantity (as, for example, a material that naturally emits a magnetic field), emit a detectable physical quantity upon external stimulation (as, for example, a material that creates a magnetic field when subjected to a current or a material that emits light when stimulated by an electric field), or reflect a detectable physical quantity; and the physical quantity can be a signal in any bandwidth of the electromagnetic spectrum (including the audio frequency range), or it can be a field such as a magnetic field. The target is scalable, in that it can be produced and sensed on a scale ranging from microscopic to macroscopic.

The sensor observes the deformation of a target affixed to a surface or embedded in a material or an object, and the deformation of the target, if any, over time. The sensor is selected to be compatible with the detectable physical quantity emitted by the target and undertakes some preprocessing of the observed physical quantity to provide data representing the physical quantity to the computer. The computer implements programs that analyze the data, and store and display the data and strain calculation in real time as the object under study is submitted to loading resulting in strain. The technology is scalable with respect to the size of the object under study.

The method in accordance with the present invention employs correlation of the sub-images of one of several SSRs or the correlation of identified sub-images in a non-SSR symbol applied to a surface. The correlation can be optical, acoustical, magnetic, or electromagnetic.

Other objects, features and advantages of the present invention will be apparent to those skilled in the art upon a reading of this specification including the accompanying drawings.

BRIEF DESCRIPTION OF THE DRAWINGS

The invention is better understood by reading the following Detailed Description of the Preferred Embodiments with reference to the accompanying drawing figures, in which like reference numerals refer to like elements throughout, and in which.

DETAILED DESCRIPTION OF THE INVENTION

In describing preferred embodiments of the present invention illustrated in the drawings, specific terminology is employed for the sake of clarity. However, the invention is not intended to be limited to the specific terminology so selected, and it is to be understood that each specific element includes all technical equivalents that operate in a similar manner to accomplish a similar purpose.

Figure 1:
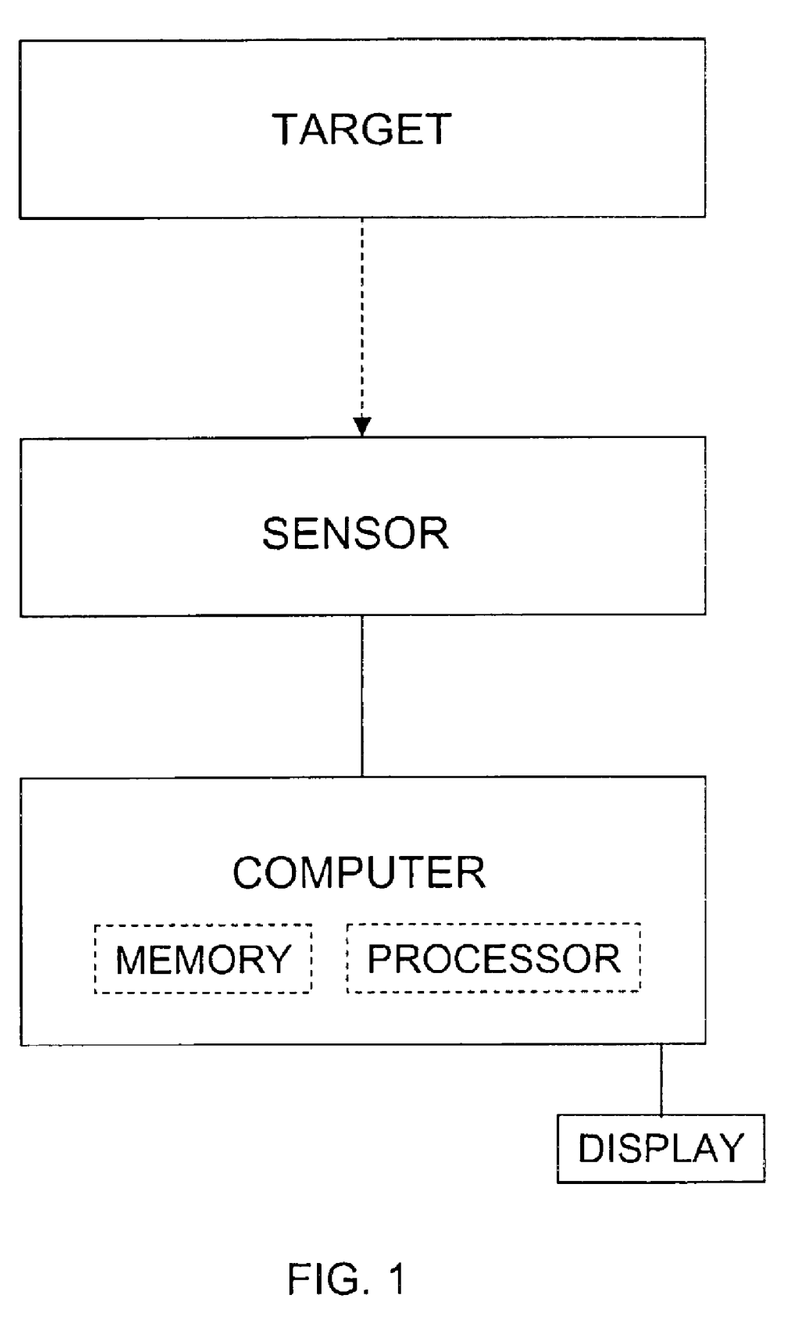
FIG. 1 is a diagrammatic view of a compressed symbology strain gage in accordance with the present invention.
Figure 2A:
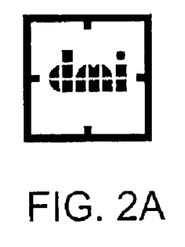
FIG. 2A shows a manufactured image configuration for a symbolic strain rosettes capable of serving as a target that satisfies the conditions for optically detecting strain when affixed to a surface undergoing load and deformation.
Figure 3:
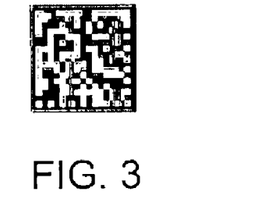
FIG. 3 shows an overall image in the form of a Data Matrix symbol, in which is included a manufactured image configuration for symbolic strain rosettes capable of serving as a target that satisfies the conditions for optically detecting strain when the affixed to a surface undergoing load and deformation.

Referring now to FIG. 1, there is shown diagrammatically a compressed symbology strain gage in accordance with the present invention, comprising a target, a sensor, and a computer. The target is a symbolic strain rosette ("SSR") that has been manufactured or identified. There are an infinite number of image configurations for the SSR. Two examples of targets in accordance with the present invention are shown in FIGS. 2A and 3. FIG. 2A is an SSR that contains a corporate logo as part of the symbol geometry, while FIG. 3 is a two-dimensional bar code that incorporates an SSR. Both SSRs are examples of targets that satisfy the conditions for optically detecting strain when affixed to a surface undergoing load and deformation.

Whether manufactured or identified, the SSR is defined in terms of its physical dimensions. Engineering strain is a measure of the relative change in length per unit length of the end points of a line segment connecting the points relative to a reference configuration of the SSR. This reference configuration is usually taken to be an undeformed position (zero loading). Any quantity in an SSR used as a strain gage must identify a geometrical property that can describe a point. An example of such a point is the centroid of a group of symbols as shown in FIG. 3. Any other point that can be uniquely identified can be considered as a property of the SSR for the purpose of strain measurement. Therefore, since the strain is measured for many possible configurations of an SSR, the end points of the same line must be identified for all possible configurations.

Figure 4:
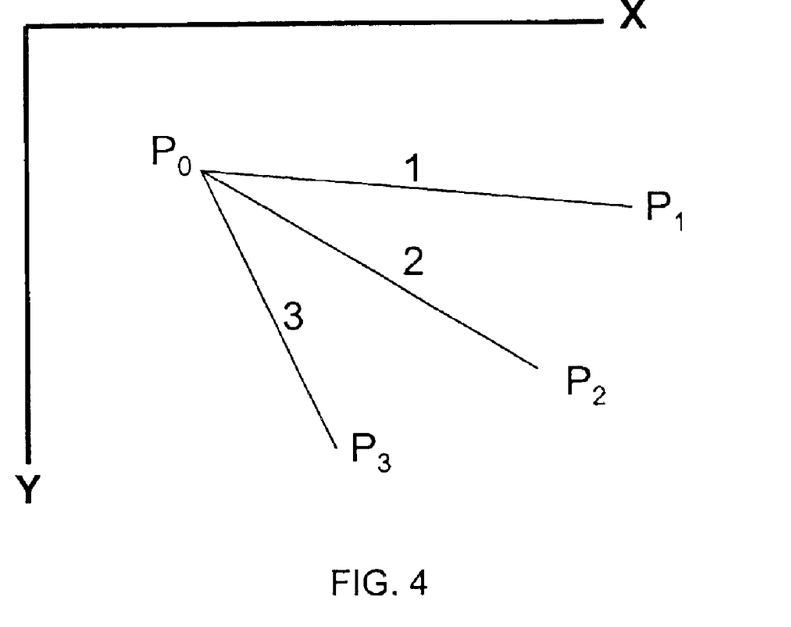
FIG. 4 shows three intersecting line segments that define a strain rosette.

A strain rosette is defined in terms of a pattern of three intersecting line segments, as shown in FIG. 4. The length of line segment 1 is measured by the end points $P_0$ and $P_1$, the length of line segment 2 is measured by the end points $P_0$ and $P_2$, and the length of line segment 3 is measured by end points $P_0$ and $P_3$.

Figure 2B:
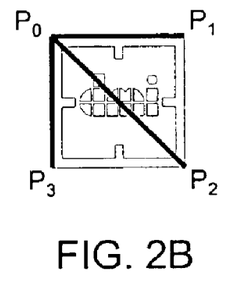
FIG. 2B shows the line segments and endpoints that define the symbolic strain rosette of FIG. 2A.

When the definition of strain is applied to the compressed symbol of the SSR, then it is necessary to identify the line segments by the location of the endpoints. The SSR shown in FIG. 2A is defined by the corner points of its outside boundary. FIG. 2B illustrates the line segments and endpoints for the SSR shown in FIG. 2A. The end points are defined by the corner points of the square boundary.

An SSR that is defined a posteriori can be identified either by centroidal coordinates or by some other convenient geometry that locates three intersecting line segments that define a strain rosette.

In one embodiment of the invention, as shown in FIG. 3, the overall image is a "two dimensional bar code" of the type developed by NASA to identify and track space shuttle parts, and the SSR is part of the information contained in the two dimensional bar code. The bar code pattern can be used to encode inventory data or a history of the object to which it is attached, as described in "A White Paper on Two Dimensional Symbols," by Paul Mathans et al. (CSPI Vision Systems 1996). However, the target does not have to contain any inventory or history data to be read.

The "two-dimensional bar code" is more formally referred to as a matrix code, a term that applies to two-dimensional codes that code data based on the position of black modules within a matrix. All of the black modules are the same dimension and it is the positions of the modules that code the data. Data Matrix is a type of two-dimensional matrix code containing dark and light square data modules. It is designed to pack a lot of information in a very small space; a Data Matrix symbol can store between one and 3116 numeric or 2335 alphanumeric characters. A Data Matrix symbol has a finder pattern of two solid lines and two alternating dark and light lines on the perimeter of the symbol. These patterns are used to indicate both orientation and printing density of the symbol. A two-dimensional imaging device such as a CCD camera is used to scan the symbology.

The information in a Data Matrix symbol is encoded by absolute dot position rather than relative dot position. While a Data Matrix symbol is easily scalable between a 1-mil square to a 14-inch square, the actual limits are dependent on the fidelity of the marking device and the optics of the sensor. Data Matrix symbols can be used for small item marking applications using a wide variety of printing and marking technologies.

Additional information regarding Data Matrix code is disclosed in U.S. Pat. Nos. 4,939,354; 5,053,609; 5,124,536.

In the case of the SSR incorporated into the two-dimensional bar code as shown in FIG. 3, the SSR is defined in terms of the centroidal coordinates of the sub-images of the bar code, as discussed in greater detail hereinafter, and can be monitored by the sensor to correlate the movement of the centroids of the sub-images of the SSR.

In another embodiment, the linear quantities that define the strain rosette can be created using linear-edged shapes or curved-edged shapes. Circles can be used to create curved-edged SSRs.

The target can be associated with an object by any means that results in the deformation of the SSR with the deformation under load. The deformation of the SSR and the object must bear a one-to-one relationship. The target can be associated with an object for which strain is to be measured by applying it directly or indirectly to the surface of the object, or by identifying it in a pre-existing pattern that defines an SSR. Whether applied or identified, the target can be embedded in the object for which strain is to be measured.

Examples of application of a target include, but are not limited to:

1. Application to a medium such as a polymide film that is bonded, for example by gluing, to the surface of the object for which strain is to be measured (indirect application);
2. Etching on a surface (direct application);
3. Painting on surface (direct application); and
4. Printing on a surface (direct application).

Target applications are described in detail in NASA STD 6002 and Handbook 6003.

Examples of identification of a target include, but are not limited to:

1. Identification by observing naturally-occurring surface features of the object that define an SSR on a macroscopic or microscopic scale (for example, features on the surface of the earth).
2. Identification by observing naturally-occurring subsurface features of the object that define an SSR on a macroscopic or microscopic scale (for example, a fossil buried in the earth).
3. Identification by observing manmade surface features of the object that define an SSR on a macroscopic or microscopic scale (for example, a collection of components).

4. Identification by observing manmade subsurface features of the object that define an SSR on a macroscopic or microscopic scale(for example, structural elements of a spacecraft covered with a skin, the structural elements of a bridge covered with a skin, or the structural elements of a building having a surface opaque in the visible spectrum).

Examples of embedding of a target include, but are not limited to:
1. Embedding in the object to be studied when the object is being formed;
2. Identification of naturally occurring or manufactured subsurface features;
3. Covering with an overlying material, such as one or more layers of paint; and
4. Implanting in a human body, in a body part or an implant. For example, if the target is affixed to a critical area of a hip joint or a hip implant, or to an artificial heart valve, the target can be viewed through the tissue surrounding the target by an x-ray sensor, and the strain and fatigue damage to the associated body part or implant can be assessed over time.

The target can naturally emit a detectable physical quantity, create a detectable physical quantity, or reflect a detectable physical quantity. The detectable physical quantity can be a signal in any portion of the electromagnetic spectrum (including the audio frequency range), or it can be a field such as a magnetic field. The detectable physical quantity can be a signal that can be characterized as a gray-scale image that can be converted into a bitmap file. Sensors that will sense various detectable physical quantities, including all these signals and fields, are commercially available.

Figure 7:
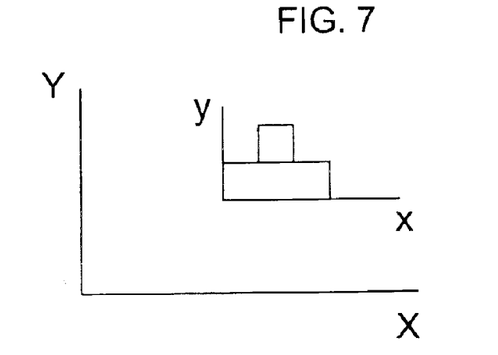
FIG. 7 is a sub-image of the strain rosette shown in FIG. 6A.
Figure 8:
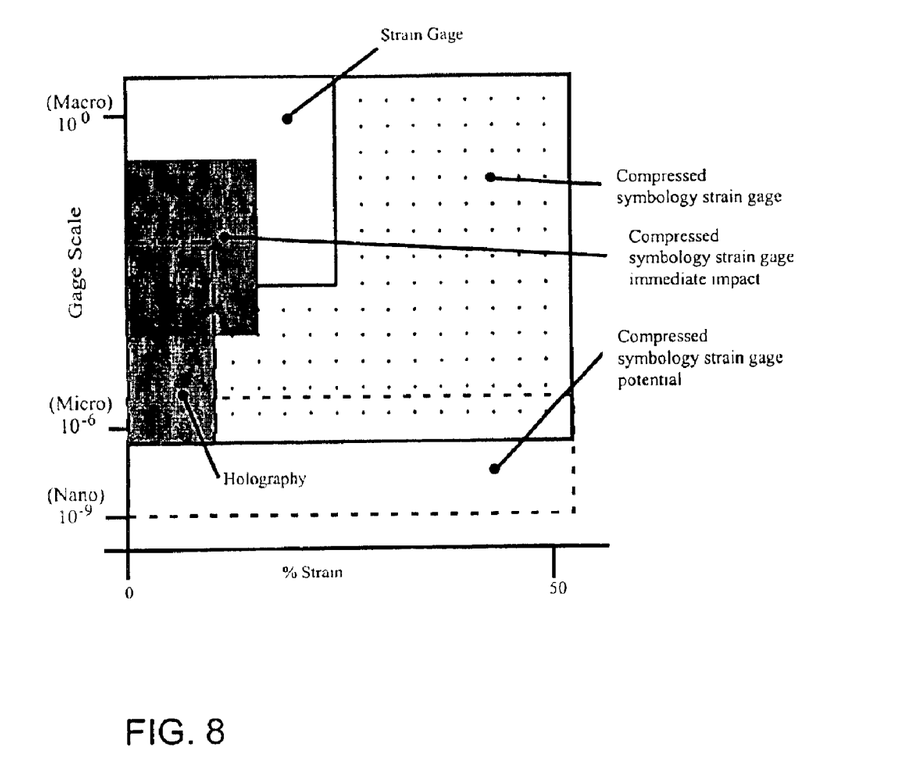
FIG. 8 is a graph showing the range of applicability of the current technology and contrasts the technology with other methods of measuring strain.

The target is scalable, in that it can be produced and sensed on a scale ranging from microscopic to macroscopic. Thus, the compressed symbology strain gage in accordance with the present invention is applicable to very large applications such as viewing a target on earth from space to determine displacements/strain of the earth's surface or subsurface strains. All that is required is to match the sensor to the size of the target image and the detectable physical quantity emitted by the target. FIG. 7 shows the range of applicability of the compressed symbology strain gage in accordance with the present invention and contrasts the compressed symbology strain gage with other methods of measuring strain.

One advantage of the compressed symbology strain gage is that strain is measured directly, as opposed to being inferred from secondary measurements using analog techniques; thus making possible an explicit detectable "reading" of normal and shear strain components. This in turn leads to greater accuracy and reduced system errors.

Another advantage of the compressed symbology strain gage is that the range of strain measurements is easily from 0 to at least 50%, which permits measurements of strain in elastic materials such as rubber and plastic. The potential exits to cover measurements at the nanoscale level.

A third, and major advantage of the compressed symbology strain gage is that subsurface strains can be measured. Subsurface measurements can have special applications in man-made composites.

The compressed symbology strain gage also can be used in the assessment of fatigue damage (accumulation) in critical areas of structures or components of devices subjected to cyclic or other loadings. This is accomplished by observing the area of a component under study over a selected period of time during the normal usage of the area. The data can then be used to predict failure of the component.

The sensor observes the deformation of a target affixed to a surface or embedded in a material by capturing the total image of the target and transmitting it to the computer. The sensor is selected to be compatible with the detectable physical quantity emitted by the target and undertakes some pre-processing of the observed physical quantity to provide data representing the physical quantity to the computer. In the case of an SSR that can be monitored optically, such as an SSR incorporated into a Data Matrix symbol, the input signal to the sensor may be a grayscale image that can be converted into a bitmap file, although other inputs can be accommodated.

The computer conventionally comprises memory for storing programs and data and a processor for implementing the programs and processing the data, and is associated with a display for displaying data. As the object under study is submitted to loading resulting in strain, the computer implements programs that (1) identify the SSR and the changes therein as a function of time and change in the load, (2) translate the changes in the SSR into strain, and (3) display it in a suitable format. The display of the data can take place in real time. The technology is scalable with respect to the size of the object under study.

The SSR is monitored—by optical, magnetic, electromagnetic, acoustic, or other sensor, as appropriate—at successive periods of time, either on a continuous time, at random times triggered by an external event, or on a programmed time basis. The sub-images of the SSR are correlated over time to detect the movement of the centroids of the sub-images, and the movements are quantified and utilized in analytical expressions to determine strain in the directions of the coordinate system used corresponding to the plane of the surface under study. The movement of the centroids is detected by a program implemented by the computer in accordance with the present invention, which identifies the SSR and its sub-images, correlates the sub-images of the SSR over time, determines the displacement of the centroids of the sub-images of the SSR, and utilizes the data obtained as input for strain equations as described hereinafter and to yield and display strain in two dimensions.

The explanation that follows of the technical basis of the present invention utilizes a Cartesian coordinate system and a specific sub-image shape for illustration. However, any coordinate system and any geometric sub-image shape may be used as long as the coordinate system is consistent for the sub images of the SSR and analyses of the strain equations.

The mathematical basis of the invention is the correlation of the movement of the centroids of sub-images defining the SSR. The sub-images can be any geometric shape. In the example shown in FIG. 5A, which is for purposes of illustration only and is not intended to limit the scope of the invention, the sub-image consists of one unit cell, which is a rectangle having a height h and a width b. Where the sub-image comprises more than one unit cell, the unit cells can be combined into, for example, a T shape (shown in FIG. 5B) consisting of a large rectangle and a small rectangle arranged next to each other, where the small rectangle is a single unit cell and the large rectangle is made up of k unit cells, where k is an integer (i.e., the size of the large rectangle is an integer multiple of the size of the small rectangle).

Figure 5A:
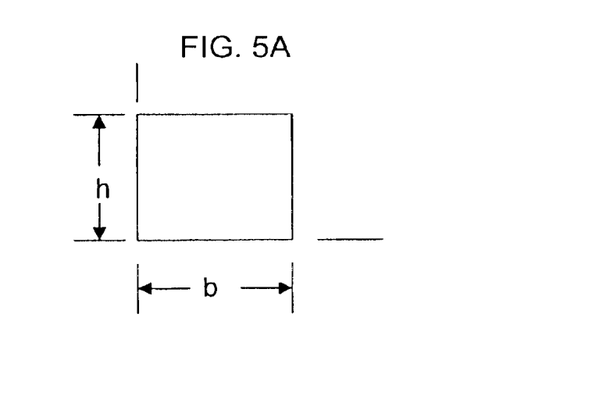
FIG. 5A shows a rectangular unit cell of a sub-image of a strain rosette.
Figure 5B:
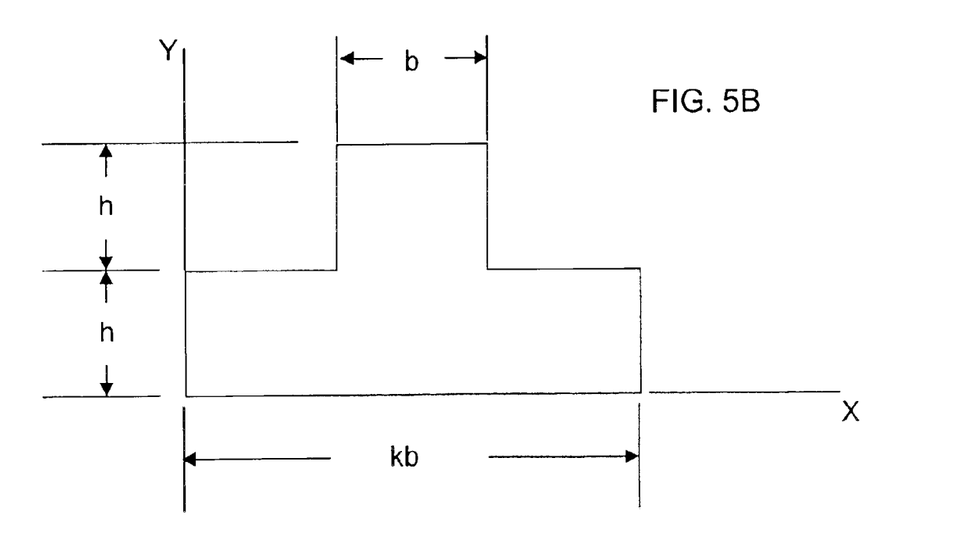
FIG. 5B shows a T-shaped sub-image of a strain rosette.
Figure 6A:
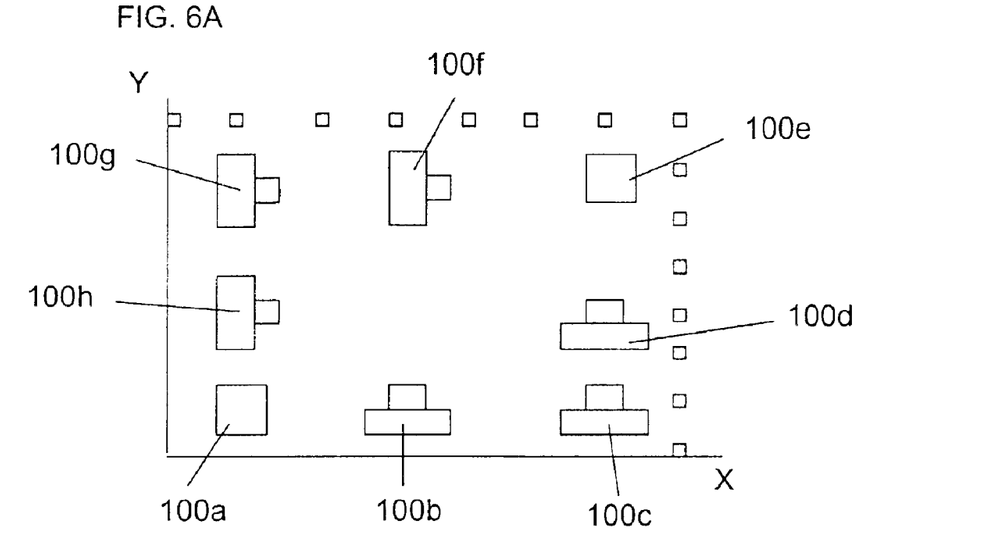
FIG. 6A shows the SSR in the Data Matrix symbol of FIG. 3.
Figure 6B:
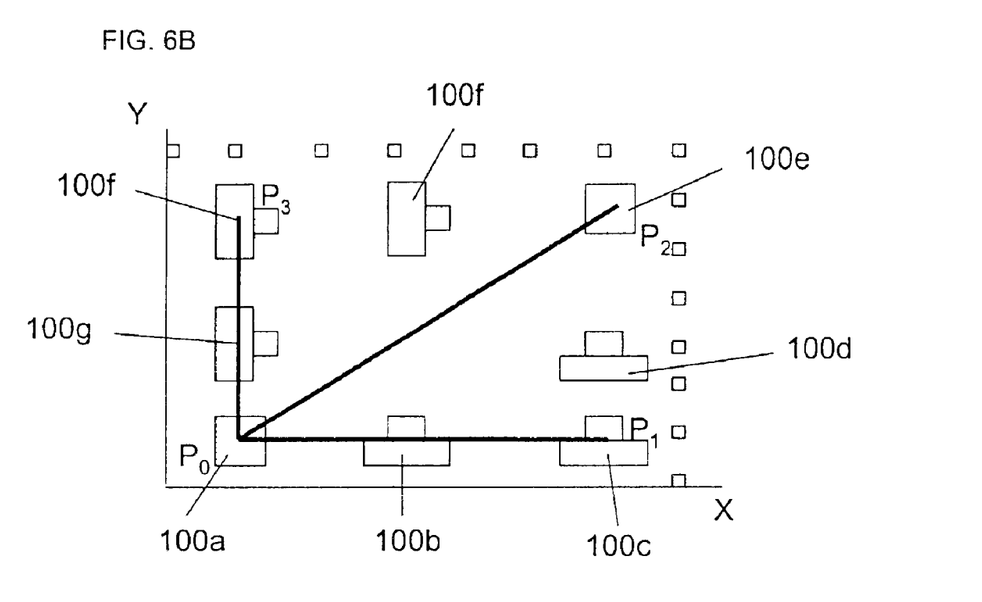
FIG. 6B shows the line segments and endpoints that define the symbolic strain rosette in the overall image shown in FIG. 3.

Taking as an example a target in which the SSR comprises a Data Matrix symbol, the pattern shown in FIG. 6A defined by the sub-images $100a$–$100h$ forms the elements of a strain rosette. In this example, sub-image $100a$ is the reference and consists of one cell of the type shown in FIG. 5A; sub-images $100b$, $100c$, and $100d$ are complex sub-images of the type shown in FIG. 5B, and primarily measure movement in the X direction; sub-image 110e, which like sub-images 100a consists of a single cell, measures movement in the X and Y directions; and sub-images 100f, 100g, and 100h are complex sub-images that measure movement in the Y direction. A minimum configuration requires the four corner sub-images, sub-images 100a, 100c, 100e, and 100g. In the example, sub-images 100a–100h form an over-determined set for the strain rosette.

The centroidal coordinates for each sub-image shown in FIG. 6A are measured from the origin of a local coordinate system. The centroidal coordinates are designated $X_c$, $Y_c$. The centroids for the rectangular sub-image of the type shown in FIG. 5A are:

$$X_c = \tfrac{1}{2} b \quad \text{(Equation 1)}$$

$$Y_c = \tfrac{1}{2} h \quad \text{(Equation 2)}$$

The centroids for the complex (compound rectangular) sub-image of the type shown in FIG. 5B are:

$$X_c = \tfrac{1}{2} kb \quad \text{(Equation 3)}$$

$$Y_c = \Sigma Y_i A_i / \Sigma A_i \quad \text{(Equation 4)}$$

Therefore $$Y_c = \frac{\left(\tfrac{h}{2}\right)(kbh) + \left(h + \tfrac{h}{2}\right)(bh)}{kbh + bh} \quad \text{(Equation 5)}$$

$$Y_c = \frac{\tfrac{1}{2} bkh^2 + \tfrac{3}{2} bh^2}{bh(k+1)} \quad \text{(Equation 6)}$$

$$Y_c = \frac{h(k+3)}{2(k+1)} \quad \text{(Equation 7)}$$

It can be shown that as k gets large, $(k+3) \cong k$, and $(k+1) \cong k$. Thus, $Y_c \cong \tfrac{1}{2} h$ and the contribution of the smaller rectangle in the complex sub-image is small.

With reference to FIG. 7, X and Y are the global coordinates of a two-dimensional sub-image. The computer will implement a scanning algorithm that locates the corner of each sub-image. If the sub-image of an SSR is denoted by its ith number, then the centroid of each sub-image is denoted as:

$$X_{ic} = X_i + X_c \text{ and} \quad \text{(Equation 8)}$$

$$Y_{ic} = Y_i + Y_c, \quad \text{(Equation 9)}$$

where $X_{ic}$ and $Y_{ic}$ are the global coordinates of the centroid of the symbol, and $X_c$ and $Y_c$ are the local centroidal coordinates of each sub-image of the symbol. For a rectangular sub-image:

$$X_{ic} = X_i + \tfrac{1}{2} b \text{ and} \quad \text{(Equation 10)}$$

$$Y_{ic} = Y_i + \tfrac{1}{2} h \quad \text{(Equation 11)}$$

and for a compound rectangular sub-image of the symbol such as the sub-image shown in FIG. 7:

$$X_{ic} = X_i + \tfrac{1}{2} kb \text{ and} \quad \text{(Equation 12)}$$

$$Y_{ic} = Y_i + \frac{h(k+3)}{2(k+1)} \quad \text{(Equation 13)}$$

Equations 12 and 13, as an example, can now be used to continue to explain by an example an optical method in accordance with the present invention for strain determination. As previously discussed, the deformation of the SSR and the deformation under load of the object to which it is applied or on which it is identified must bear a one-to-one relationship. Using the example of the SSR incorporated in the Data Matrix symbol of FIG. 3, a 5×5 pixel array is selected for each cell and the strain rosette will have a 100-pixel subset for each sub-image. The following calculations relate the change, ΔS, in the centroids of the sub-images, with the strain induced by loading the surface under study.

$$\Delta S_i = [\Delta X_i^2 + \Delta Y_i^2]^{1/2} \quad \text{(Equation 14)}$$

$$\Delta S_i = [(X_{i+1} - X_1)^2 + (Y_{i+1} - Y_1)^2]^{1/2} \quad \text{(Equation 15)}$$

$$\Delta S_i' = [(X'_{i+1} - X'_1)^2 + (Y'_{i+1} - Y'_1)^2]^{1/2} \quad \text{(Equation 16)}$$

$$l_i = \frac{(X_{i+1} - X_1)}{[(X_{i+1} - X_1)^2 + (Y_{i+1} - Y_1)^2]^{1/2}} \quad \text{(Equation 17)}$$

$$m_i = \frac{(Y_{i+1} - Y_1)}{[(X_{i+1} - X_1)^2 + (Y_{i+1} - Y_1)^2]^{1/2}} \quad \text{(Equation 18)}$$

$$\tfrac{1}{2}[(\Delta S'/\Delta S)^2 - 1] = l_i^2 \epsilon_{xx} + m_i^2 \epsilon_{yy} + 2 l_i m_i \epsilon_{xy} \quad \text{(Equation 19)}$$

$$\tfrac{1}{2}[(\Delta S'/\Delta S)^2 - 1] = (\Delta X_i/\Delta S_i)^2 \epsilon_{xx} + (\Delta Y_i/\Delta S_i)^2 \epsilon_{yy} + 2(\Delta X_i/\Delta S_i)(\Delta Y_i/\Delta S_i) \epsilon_{xy} \quad \text{(Equation 20)}$$

where l and m are direction cosines and l=m=0.707 in this example for the coordinate system and symbol used.

The above relationships allow the determination of $\epsilon_{xx}$, $\epsilon_{yy}$, $\epsilon_{xy}$ from the SSR used in this example. Similarly, an SSR in accordance with the present invention can be devised for any coordinate system or can be identified by analysis of a pre-existing symbol or other pattern so that it can be used as a target in the method in accordance with the present invention. The movement of the centroids of the sub-images of the target can be utilized with the strain equations written for the coordinate system used to determine strain optically and the computer program in accordance with the present invention is applicable to any coordinate system and sub-image geometric shape.

Figure 9:
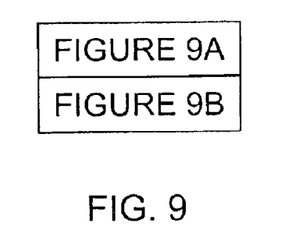
FIG. 9 shows the arrangement of FIGS. 9A and 9B.
Figure 9A:
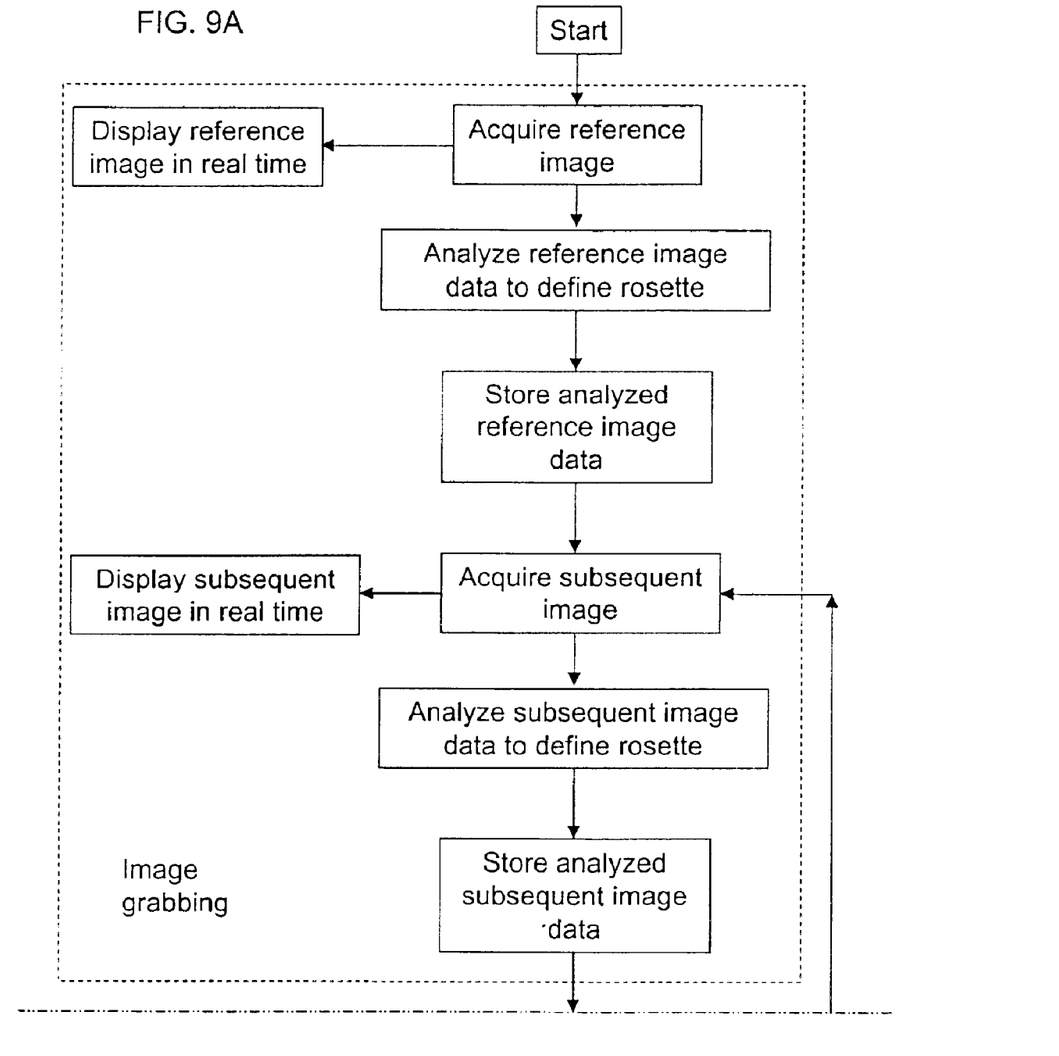
FIGS. 9A and 9B together are a high level flow diagram illustrating the algorithm followed by the computer program in accordance with the present invention.
Figure 9B:
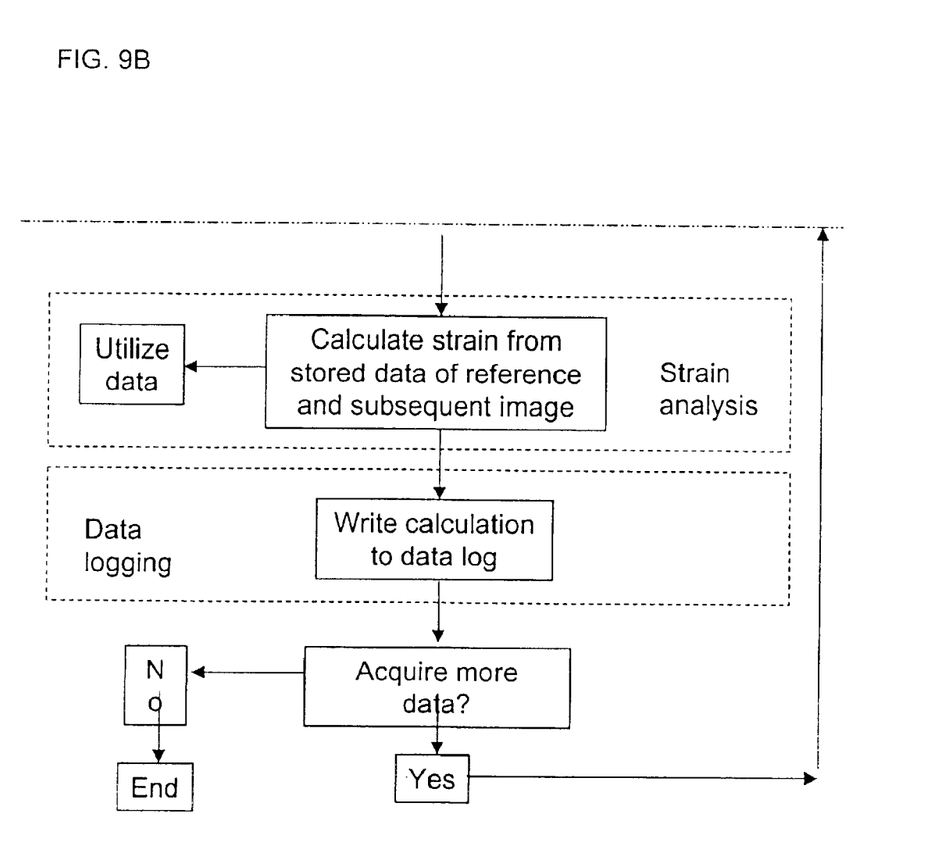

Referring now to FIGS. 9A and 9B together, there are shown a high level flow diagram illustrating the algorithm followed by the computer programs in accordance with the present invention. The algorithm comprises three basic stages, image grabbing, strain analysis, and data logging; and utilizes two types of images, a reference image, acquired either without application of a load or with a reference load on the object for which strain is to be measured, and subsequent images, acquired after the reference image in the presence of a load or change to the load on the object.

The image grabbing stage comprises the following steps: The sensor acquires the reference image and outputs data representing the reference image to the computer. A program or programs implemented by the computer then analyzes the reference image data to define an SSR, and concurrently displays the reference image, preferably in real time, on a computer monitor or other display device. Following the analysis step, the computer stores the analyzed reference image data. Once the reference image has been acquired, analyzed, and stored, the sensor acquires a subsequent image and outputs data representing that subsequent image (that is, the current subsequent image) to the computer.

Acquisition of subsequent images can take place either continuously or at predetermined intervals, or it can be triggered by an external event such as the application of a load. The number of subsequent images thus can range from one to thousands. Once data representing a subsequent image is input to the computer, the program analyzes it to define an SSR, and concurrently displays the corresponding subsequent image, preferably in real time, on a computer monitor or other display device (preferably on the same monitor or other display device on which the reference image is being displayed, to facilitate comparison). Following the analysis step, the computer stores the analyzed subsequent image data for the current subsequent image.

The strain analysis stage takes place following the image grabbing stage, and is carried out each time a subsequent image is acquired. In the strain analysis stage, the computer calculates the strain from the stored reference image data and the stored subsequent image data for the current subsequent image, based on the changes in the SSR as a function of time and change in the load. Thus, a new strain calculation is made for each subsequent image. The strain calculation can then be utilized as a display, as well as providing information on fatigue damage or strain hysteresis for materials of known and unknown mechanical properties, providing advance notice of an approaching failure point for materials of known mechanical properties, extrapolating a failure point for a material of unknown mechanical properties, or based on collected damage accumulation data.

The data logging stage takes place following each iteration of the strain analysis stage. In the data logging stage, the program gets the current results and writes them to a log file.

As will be appreciated by those of skill in the art, the flow diagram of FIGS. 9A and 9B is for purposes of illustration, and some changes can be made in the algorithm without affecting the results. For example, the display of the reference and subsequent images can take place sequentially with the analysis of those images, as well as substantially concurrently; the acquisition and display of the reference and/or the subsequent images can be initiated by an external event; and images can be recorded during an event and stored for processing at a later time.

Modifications and variations of the above-described embodiments of the present invention are possible, as appreciated by those skilled in the art in light of the above teachings. It is therefore to be understood that, within the scope of the appended claims and their equivalents, the invention may be practiced otherwise than as specifically described.

We claim:

1. A compressed symbology strain gage comprising:
    a target comprising a symbolic strain rosette in the form of a compressed symbol that is defined in terms of the end points of three intersecting line segments that define a strain rosette, the target being associated with a body for which at least one of strain and fatigue damage is to be measured and emitting a detectable physical quantity;
    sensor means for pre-processing the detectable physical quantity emitted by the target and output data representing the physical quantity, the sensor means being compatible with the detectable physical quantity;
    means for analyzing the data output by the sensor means to define the symbolic strain rosette; and
    means for measuring the strain on the body directly based on the pre-processed and analyzed data.

2. A method of measuring at least one of strain and fatigue damage on an object directly, comprising the steps of:
    associating a symbolic strain rosette with an object in such a way that deformation of the symbolic strain rosette and deformation under load of the object bear a one-to-one relationship, wherein the symbolic strain rosette is in the form of a compressed symbol that is defined in terms of the end points of three intersecting line segments that define a strain rosette;
    identifying the changes in the symbolic strain rosette as a function of time and change in the load applied to the object; and
    translating the changes in the symbolic strain rosette into a direct measurement of strain.

3. The method of claim 2, wherein the symbolic strain rosette is defined a priori by manufacture and the associating step comprises applying the symbolic strain rosette to the object.

4. The method of claim 2, wherein the associating step comprises identifying the symbolic strain rosette a priori.

5. The compressed symbology strain gage of claim 1, wherein the symbolic strain rosette is defined a priori by manufacture.

6. The compressed symbology strain gage of claim 5, wherein the symbolic strain rosette a strain rosette contained in a two dimensional bar code.

7. The compressed symbology strain gage of claim 6, wherein the two dimensional bar code is a Data Matrix symbol.

8. The compressed symbology strain gage of claim 1, wherein the target is identified in a pre-existing pattern that defines the symbolic strain rosette.

9. The compressed symbology strain gage of claim 1, further comprising means for utilizing the strain measurement to provide information on at least one of fatigue damage and strain hysteresis for materials of known and unknown mechanical properties.

10. The compressed symbology strain gage of claim 1, further comprising means for utilizing the strain measurement to provide advance notice of an approaching failure point for materials of known mechanical properties.

11. The compressed symbology strain gage of claim 1, further comprising means for utilizing the strain measurement to extrapolate a failure point for a material of unknown mechanical properties.

12. The compressed symbology strain gage of claim 1, further comprising means for utilizing the strain measurement based on collected damage accumulation data.

13. The method of claim 2, further comprising the step of utilizing the strain measurement to provide information on at least one of fatigue damage and strain hysteresis for materials of known and unknown mechanical properties.

14. The method of claim 2, further comprising the step of utilizing the strain measurement to provide advance notice of an approaching failure point for materials of known mechanical properties.

15. The method of claim 2, further comprising the step of utilizing the strain measurement to extrapolate a failure point for a material of unknown mechanical properties.

16. The method of claim 2, further comprising the step of utilizing the strain measurement based on collected damage accumulation data.

* * * * *